(12) United States Patent
Tanaka

(10) Patent No.: US 6,973,209 B2
(45) Date of Patent: Dec. 6, 2005

(54) DEFECT INSPECTION SYSTEM

(75) Inventor: Toshihiko Tanaka, Komagane (JP)

(73) Assignee: Olympus Optical Co., Ltd., Tokyo (JP)

(*) Notice: Subject to any disclaimer, the term of this patent is extended or adjusted under 35 U.S.C. 154(b) by 739 days.

(21) Appl. No.: 09/917,845

(22) Filed: Jul. 25, 2001

(65) Prior Publication Data

US 2002/0009220 A1 Jan. 24, 2002

Related U.S. Application Data

(63) Continuation of application No. PCT/JP00/08372, filed on Nov. 28, 2000.

(30) Foreign Application Priority Data

Nov. 29, 1999 (JP) ................................. 11-338425

(51) Int. Cl.⁷ .............................................. G06K 9/00
(52) U.S. Cl. ...................... 382/149; 382/141; 382/145; 382/147; 348/125; 702/35
(58) Field of Search .................. 382/141, 145, 382/147, 149, 144; 348/86, 87, 125; 702/35, 702/81, 82; 250/559.01; 356/237.1, 237.2, 356/237.3, 237.4, 237.5; 700/121

(56) References Cited

U.S. PATENT DOCUMENTS

| | | | | |
|---|---|---|---|---|
| 5,440,649 A | * | 8/1995 | Kiyasu et al. | ............... 382/147 |
| 5,694,214 A | | 12/1997 | Watanabe et al. | |
| 5,943,437 A | | 8/1999 | Sumie et al. | |
| 5,963,314 A | | 10/1999 | Worster et al. | |
| 6,248,988 B1 | | 6/2001 | Krantz | |
| 6,330,352 B1 | | 12/2001 | Ishikawa et al. | |
| 6,400,839 B1 | | 6/2002 | Takayama | |
| 6,438,438 B1 | * | 8/2002 | Takagi et al. | ............... 700/121 |
| 6,456,951 B1 | | 9/2002 | Maeda et al. | |
| 6,597,381 B1 | * | 7/2003 | Eskridge et al. | ............. 345/804 |
| 2002/0024659 A1 | | 2/2002 | Tanaka | |

FOREIGN PATENT DOCUMENTS

| | | |
|---|---|---|
| JP | 4-285845 A | 10/1992 |
| JP | 5-45300 A | 2/1993 |
| JP | 6-341960 A | 12/1994 |
| JP | 8-147408 A | 6/1996 |

(Continued)

OTHER PUBLICATIONS

Official Action dated Mar. 15, 2002 issued in counterpart Singapore application No. SG 200104489-0, filed Nov. 28, 2000.

*Primary Examiner*—Bhavesh M. Mehta
*Assistant Examiner*—John Strege
(74) *Attorney, Agent, or Firm*—Frishauf, Holtz, Goodman & Chick, P.C.

(57) ABSTRACT

A defect inspection system is provided which comprises an image acquiring section for acquiring a two-dimensional image of a subject which is a processing target in a manufacturing process, a defect extracting section for extracting a defect by a defect extraction algorithm using a predetermined parameter for an image acquired by the image acquiring section, a displaying section for displaying an image of a defect of the subject extracted by the defect extracting section, a parameter adjusting section for adjusting the parameter in accordance with a defect extraction degree for the subject, and a quality judging section for judging the quality of the subject based on a defect information extracted by the defect extracting section.

16 Claims, 4 Drawing Sheets

FOREIGN PATENT DOCUMENTS

| | | | |
|---|---|---|---|
| JP | 8-278256 A | 10/1996 |
| JP | 8-321700 A | 12/1996 |
| JP | 9-61365 A | 3/1997 |
| JP | 9-145633 A | 6/1997 |
| JP | 11-194996 A | 7/1999 |
| JP | 11-195105 A | 7/1999 |

* cited by examiner

DEFECT INSPECTION SYSTEM

CROSS-REFERENCE TO RELATED APPLICATIONS

This is a Continuation Application of PCT Application No. PCT/JP00/08372, filed Nov. 28, 2000, which was not published under PCT Article 21(2) in English.

This application is based upon and claims the benefit of priority from the prior Japanese Patent Application No. 11-338425, filed Nov. 29, 1999, the entire contents of which are incorporated herein by reference.

BACKGROUND OF THE INVENTION

1. Field of the Invention

The present invention relates to a defect inspection system which inspects defects on a surface of, e.g., a semiconductor wafer, an LCD substrate or a print wiring board.

2. Description of the Related Art

In general, in the middle of a semiconductor wafer manufacturing process, a product having the patterned resist provided through a film forming layer is formed on a substrate consisting of silicon.

However, in a photolithography process, irregularities of a film or attachment of dusts existing on the resist applied on the surface of the substrate can be a cause of occurrence of defects such as a defective line width of a pattern or generation of a pin hole in the pattern after etching.

Thus, in the substrate manufacturing process before etching, an inspection of existence/absence of defects is usually carried out for all the substrates. As such a method for inspecting all the substrates, a method by which an inspector visually observes the surface of the substrate is often conducted. However, according to the method of visually observing the substrate by the inspector in this manner, a difference in judgment between inspectors or an influence of dust coming out from a body of the inspector can not be ignored. Therefore, in recent years, there is considered a defect inspection system which can eliminate a difference in judgment between inspectors and at the same time inspect defects of the substrate from the outside of a clean room.

In such a defect inspection system, in order to eliminate a difference in judgment by inspectors, a recipe for determining extraction or a degree of defects is created in advance, and a surface defect is detected in accordance with this recipe. In creation of this recipe, for example, one arbitrary substrate in an inspection lot is imaged by a CCD camera, and the picked-up two-dimensional image is subjected to image processing, thereby extracting respective defects such as flaws, unevenness or dust. An inspector determines a parameter so that the quality judgment can be optimally carried out by confirming a degree of extraction of the defect and changing a value of the parameter for determining extraction conditions by inputting the value from an operation portion. Further, the actual defects are classified by registering defects while visually checking or observing them using a microscope and the like.

However, in creation of a conventional recipe, processing by which a value of a parameter for determining defect extraction conditions is varied in accordance with each of a plurality of substrates and a degree of extraction of a defect is then reconfirmed in the form of an image is repeated several times in accordance with each substrate, and the parameter is determined so that the quality judgment can be optimally performed. Therefore, the operation for creating the recipe takes a lot of trouble, and comparison with other substrates can be effected only in terms of values. Accordingly, there is a problem that the contents of the recipe become irregular depending on the inspectors.

An object of the present invention is to provide a defect inspection system which can easily create a recipe for extracting a defect and create the recipe with high reliability.

BRIEF SUMMARY OF THE INVENTION (1) According to the present invention, there is provided a defect inspection system comprising: image acquiring means for acquiring a two-dimensional image of a subject which is a processing target in a manufacturing process; defect extracting means for extracting a defect from an image acquired by the image acquiring means by a defect extraction algorithm using a predetermined parameter; displaying means for displaying an image of the defect of the subject extracted by the defect extracting means; parameter adjusting means for adjusting the parameter in accordance with a defect extraction degree for the subject; and quality judging means for judging the quality of the subject based on a defect information extracted by the defect extracting means.

(2) In the defect inspection system described in (1), the quality judging means has: a function of checking the defect information extracted by the defect extracting means with defect data registered in a defect dictionary to determine a type of the defect; and a function of registering new defect data in the defect dictionary.

(3) In the defect inspection system described in (1), the parameter adjusting means includes a slide switch which is displayed on a screen of the displaying means and adjusts the parameter, the slide switch and an image of the subject are simultaneously displayed on the screen of the displaying means.

(4) In the defect inspection system described in (1), the defect extracting means has a function of automatically setting a parameter to judge a subject whose defect is known in advance.

(5) In the defect inspection system described in (1), the quality judging means judges the quality of an image of the subject obtained by executing defect extraction by the defect extracting means by using the parameter set by the parameter adjusting means.

(6) In the defect inspection system described in (1), the displaying means has a function of displaying a list of images of a plurality of subjects extracted by the defect extracting means by minimizing them.

(7) In the defect inspection system described in (6), and the displaying means displays a list of thumbnail images obtained by minimizing the images.

(8) In the defect inspection system described in (7), and the displaying means displays the thumbnail image in accordance with each lot of a cassette storing therein the subject.

(9) In the defect inspection system described in (1), the displaying means displays an image of a subject determined to be defective by the quality judging means in an area different from an area for displaying images of a plurality of images extracted by the defect extracting means.

(10) In the defect inspection system described in (1), the displaying means displays a defect extracted by the defect extracting means in such a manner the defect overlaps on an image of the subject.

(11) In the defect inspection system described in (1), the displaying means displays a result obtained by the quality judgment by the quality judging means by using colors or characters for each image.

(12) In the defect inspection system described in (1), the displaying means displays the defects by distinguishing them by using different colors in accordance with each type.

(13) In the defect inspection system described in (1), the displaying means changes a color of a defect extracted by using a parameter changed by the parameter adjusting means and displays it.

(14) In the defect inspection system described in (1), the predetermined parameter is prepared in accordance with a type of defect, an inspection condition, or an inspection method.

(15) In the defect inspection system described in (1), the parameter adjusting means can set a lower limit value and an upper limit value for the predetermined parameter, the defect extracting means extracting as a defect image data which exceeds the upper limit among image data exceeding the lower limit value.

(16) In the defect inspection system described in (1), the defect extracting means has a function of registering a defect designated by the displaying means.

(17) In the defect inspection system described in (1), the displaying means has a function of displaying an image of the subject based on a parameter which has been changed by the parameter adjusting means.

(18) In the defect inspection system described in (1), the displaying means has a list box which displays types of defects, and if any one of types of defects displayed on this list box is designated, a defect corresponding to the designated type is displayed.

(19) In the defect inspection system described in (1), the displaying means redisplays an image before a parameter is changed by the parameter adjusting means if a predetermined operation is carried out.

(20) In the defect inspection system described in (1), the displaying means changes a color of frame of an image of a subject determined to be defective by the quality judging means and displays it.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently embodiments of the invention, and together with the general description given above and the detailed description of the embodiments given below, serve to explain the principles of the invention.

DETAILED DESCRIPTION OF THE INVENTION

An embodiment according to the present invention will now be described hereinafter with reference to the accompanying drawings.

Figure 1:
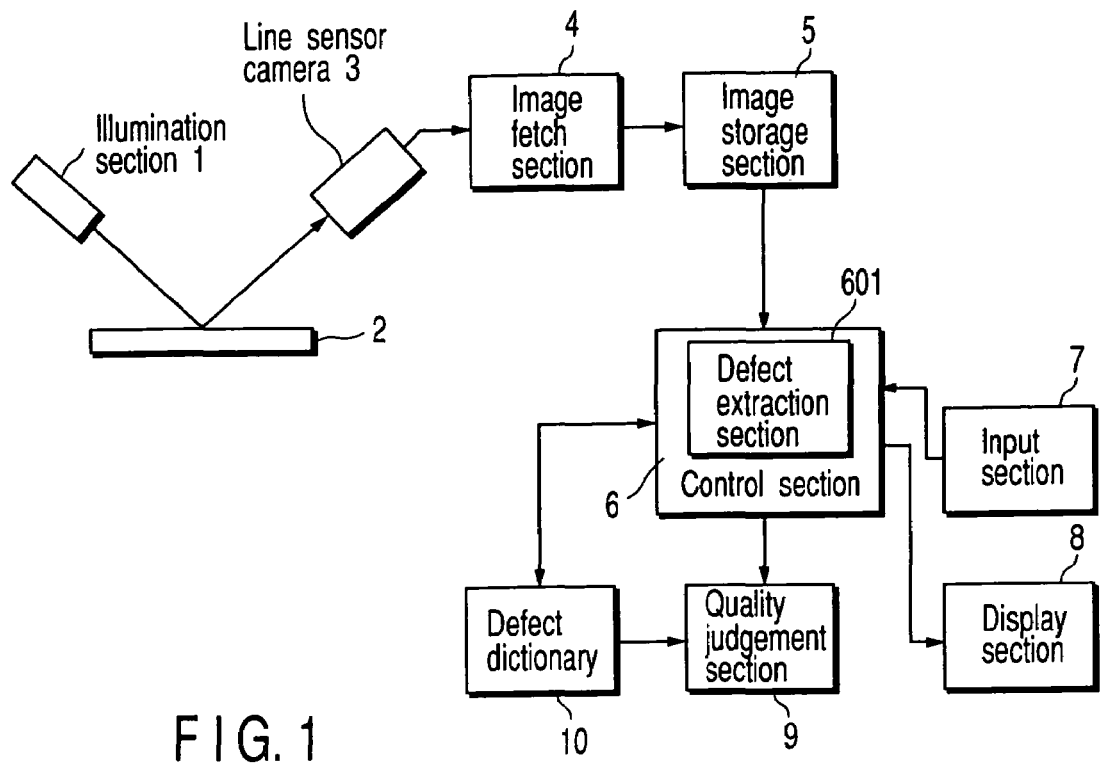
FIG. 1 is a view showing a schematic structure of a defect inspection system according to an embodiment of the present invention.

FIG. 1 is a view showing a schematic structure of a defect inspection system according to the embodiment of the present invention. In FIG. 1, an illumination section 1 illuminates an illuminating light ray at a predetermined incidence angle on a surface of a substrate 2 of a subject mounted on a stage (not shown in the figure). A line sensor camera 3 as imaging means is arranged at a position (reflection direction) opposed to the illumination section 1, and the line sensor camera 3 images a surface of the substrate 2 linearly illuminated by the illumination section 1. An image input section 4 is connected to the line sensor camera 3, and a control section 6 is connected to the image input section 4 through an image storage section 5.

An image for each one line of the surface of the substrate 2 is fetched by the line sensor camera 3 while the stage is moved in one direction, and the fetched image is inputted to the image input section 4. The image input section 4 generates a two-dimensional image of the entire surface of the substrate 2 by connecting each image for each one line imaged by the line sensor camera 3. Image data of the two-dimensional image generated by the image input section 4 is stored in the image storage section 5 and supplied to the control section 6.

The control section 6 has a defect extraction section 601. An input section 7, a display section 8, a quality judgment section 9, and a defect dictionary 10 are connected with the control section 6. The defect extraction section 601 removes an outer shape image inherent to the substrate, a specific pattern image or the like, and extracts defective parts from all the substrate images stored in the image storage section 5 based on a defect extraction algorithm using a predetermined parameter. The parameter can be changed from outside, and a degree (sensitivity) of defect extraction is adjusted by changing the parameter. In this case, the parameter consists of a coordinate (deviation) of a defect required for extracting various defects such as flaws, irregularities or dust on the surface of the substrate 2 or a pseudo defect, a distribution value, and a characteristic value of, for example, tint.

The input section 7 has buttons or sliders which are displayed on a display section 8 as will be described later. A parameter and others are inputted from the input section 7 to the defect extraction section 601 by an inspector. The display section 8 displays various kinds of images designated by the control section 6. The quality judgment section 9 checks defect information extracted by the defect extraction section 601 with defect data stored in the defect dictionary 10 to determine types of defects and the like, and carries out the quality judgment of a target substrate. The defect dictionary 10 stores various kinds of defect data such as flaws or irregularities in advance. If a new defect is found, it is registered as new defect data by a direction from the control section 6.

Figure 2:
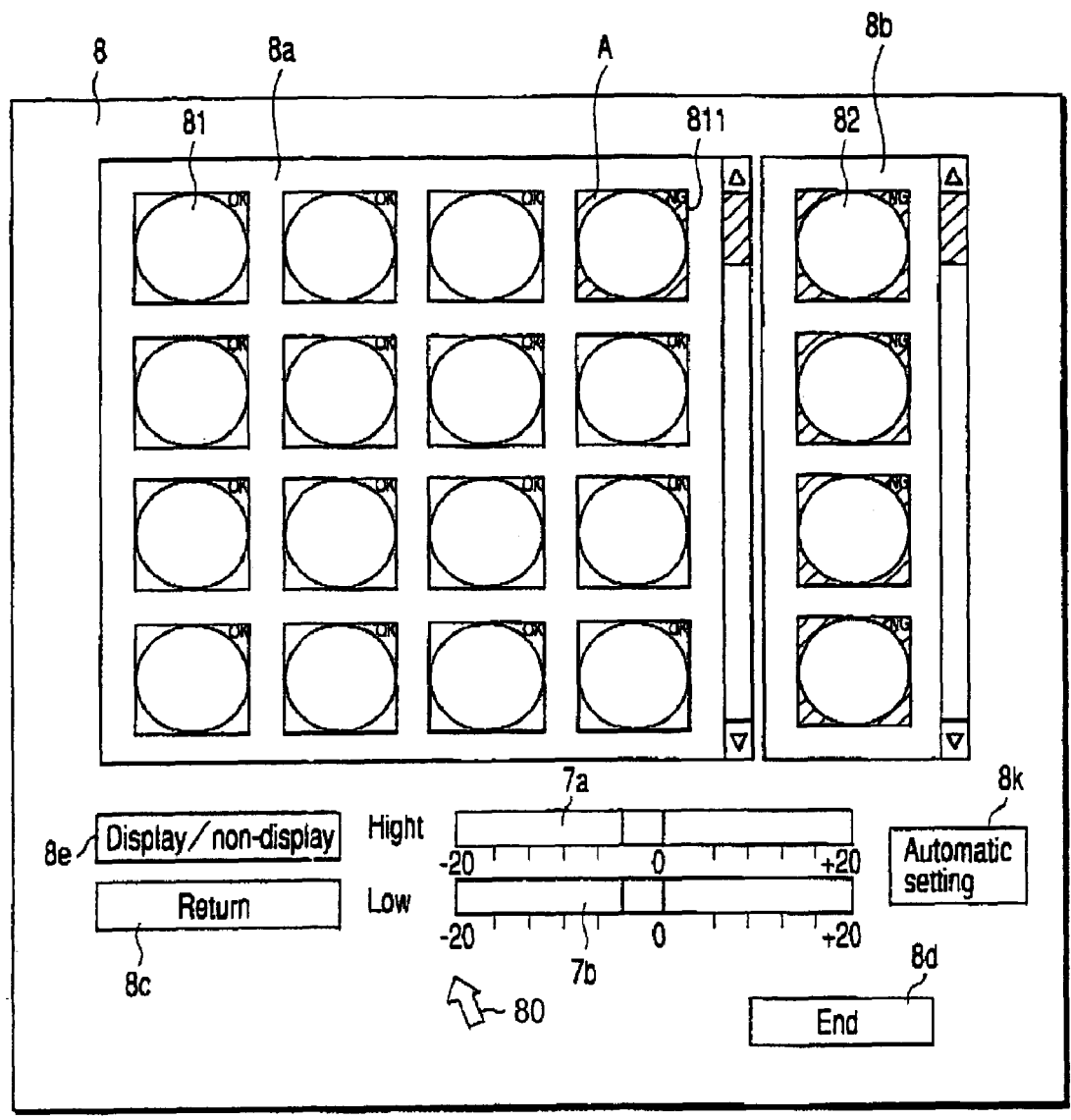
FIG. 2 is a view showing an example of screen display in a display section according to the embodiment of the present invention.

FIG. 2 is a view showing an image display example on the display section 8. Outside the image display area on the screen of the display section 8, button switches or slide switches functioning as the input section 7 are displayed. An upper limit value slide switch 7a and a lower limit value slide switch 7b are used when an inspector adjusts an upper limit value and a lower limit value of threshold values for defect extraction by changing parameters for the defect extraction section 601. The parameters may be prepared as a parameter group in accordance with each type of defects, inspection conditions, inspection methods, and extraction techniques, and a parameter for a plurality of parameters groups may be changed by the input section 7. Furthermore, the input section 7 may change parameters for detection of overlap displacement of images on a lower layer film and an upper layer film obtained by imaging using a non-illustrated microscope or for measurement of a resist cut quantity in a peripheral portion of the substrate. Moreover, the input section 7 is not limited to the one displayed on the display section 8, and it may be an external operation portion provided with a touch panel or input switches.

In the defect inspection system as above-described structure, a recipe for determining a defect extraction degree which becomes a reference of the quality judgment is created first. At first, the substrate 2 is selected in units of a recipe inspection lot in a cassette (not shown in the figure). A plurality of substrates whose defects have been already known and a plurality of non-defective substrates are included in the recipe inspection lot.

When each substrate 2 in this recipe inspection lot is imaged by the line sensor camera 3, the picked-up image is generated as a two-dimensional image by the image input section 4. Image data of this two-dimensional image is stored in the image storage section 5 and supplied to the defect extraction section 601 of the control section 6. In this case, a parameter capable of sorting a plurality of substrates with various defects which have been recognized and a plurality of non-defective substrates with defects which are not determined as NG is automatically set in the defect extraction section 601, and defect extraction is executed by the defect extraction algorithm using this parameter.

In this manner, defect extraction is carried out for all the substrate in accordance with respective lots of each cassette or each slot-selected substrate by using the defect extraction algorithm, and its result is displayed on the display section 8 as a thumbnail image as will be described later.

FIG. 2 shows a display example on the display section 8 at the time of defect extraction mentioned above. Substrate images 81 of all the substrates 2 are displayed on an area 8a on the left side of screen on the display section 8 in the order of slots or ID codes, or in the random order in the vertical and horizontal directions. Defective substrate images 82 registered as defective products in advance are displayed on an area 8b on the right side of the screen in the vertical direction.

Further, as a result of the quality judgment by the set parameter, a character "OK" representing a non-defective product or "NG" representing a defective product is displayed on each substrate image 81 on the area 8a, and the character "NG" representing a defective product is also displayed on each defective substrate image 82 shown on the area 8b. Actual defect information may be displayed on each defective substrate image 82 on the area 8b.

In this state, by using a mouse (not shown in the figure), an inspector sets a pointer 80 at a predetermined position of the thumbnail image on the display section 8 and perform the right- or left-click operation of the mouse. As a result, the thumbnail image on the area 8a or the area 8b can be enlarged or minimized to be displayed. Furthermore, when the inspector sets the pointer 80 on a specific substrate image 81 or 82 on the thumbnail screen on the area 8a or the area 8b by using the mouse and double-clicks the mouse, only the image specified by the pointer 80 can be displayed on one screen.

Incidentally, although 16 substrate images 81 are displayed on the area 8a in FIG. 2, since 25 substrates are generally loaded in one cassette, the remaining nine substrate images 81 can be also displayed. In this case, the nine substrate images 81 which are not shown in FIG. 2 can be displayed by scrolling the area 8a. Similarly, the defective substrate images 82 which are not shown in FIG. 2 can be displayed by scrolling the area 8b.

Figure 3:
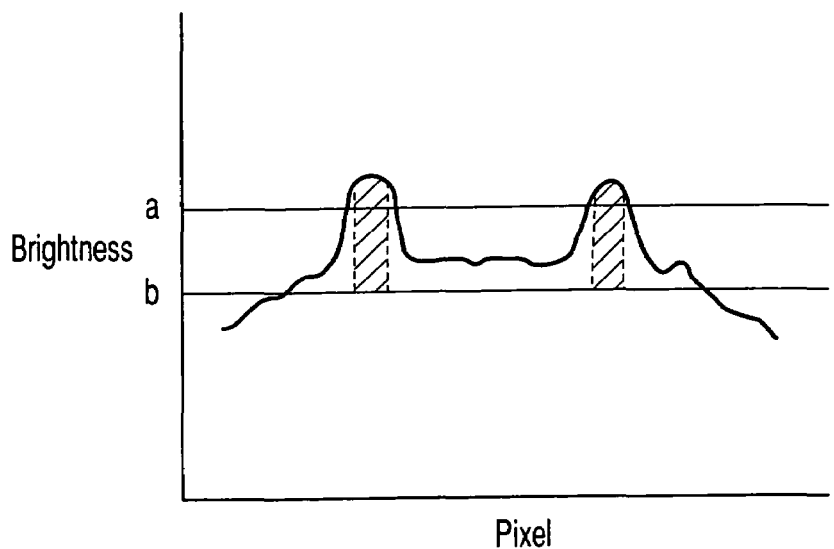
FIG. 3 is a view for explaining a threshold value for defect extraction according to the embodiment of the present invention.

Next, the inspector adjusts a parameter for determining defect extraction conditions by using the input section 7 while watching each substrate image 81 displayed as a thumbnail image. In this case, the inspector uses the mouse to carry out the sliding operation of the slide switches 7a and 7b displayed on the screen on the display section 8. Consequently, for example, as a parameter, a threshold value for an upper limit value a and a lower limit value b of the brightness for defect extraction such as shown in FIG. 3 is adjusted. Here, it is assumed that, as to the automatically set parameter, all the substrates are free from defects, the character "OK" is displayed on all the substrate screens on the thumbnail screen and the inspector thereby performs adjustment for lowering the upper limit value a.

As a result, the defect extraction section 601 newly executes the defect extraction for pixel data of all the substrates 2 stored in the image storage section 5 by the defect extraction algorithm using the newly set parameter, thereby updating the thumbnail image. This thumbnail image is updated each time the parameter is changed. In this case, specifically, it is assumed that there is the possibility of existence of a defect in the pixel data of the substrate 2 exceeding the lower limit value b shown in FIG. 3. Among the pixel data of the substrate 2 exceeding the lower limit value b, data exceeding the upper limit value a is extracted as a defect. That is, reduction and speedup of the defect extraction processing are achieved because the defect extraction is not effected for the pixel data of the substrate 2 not more that the lower limit value b.

When a defect extraction degree is increased by lower the upper limit value of the parameter in this manner, information notifying that a defect has been extracted is displayed on the substrate image 81 in which the character "OK" indicative of a non-defective product has been displayed on the area 8a, and the quality judgment is conducted for the corresponding substrate image 81. Then, the character "NG" indicative of a defective product is displayed on place of the character "OK" representing a non-defective product. In FIG. 2, the substrate image 81 to which a symbol A is given shows that state.

In this case, since the color of a frame portion 811 of the substrate image 81 which has been determined as a defective product is changed, the defective substrate can be found at a glance. In this state, when the inspector specifies a plurality of substrate images 81 determined as defective products by the drag & drop operation of the mouse or by using the pointer 80, these substrate images 81 can be altogether moved to the area 8b to be registered as defective substrates. Then, the initially set parameter is changed to perform the defect extraction of the non-defective substrate from which a defect was not able to be found. If a defect such that the substrate can not be put on the production line as a non-defective product is found, that substrate can be registered as a defective substrate. On the contrary, it is possible to cancel registration of the defective substrate image 82 which can be put on the production line as a non-defective product on the area 8b by the detailed judgment by the inspector. In this case, the substrate determined as a defective substrate before changing the parameter is displayed as a non-defective substrate.

Incidentally, when the inspector uses the mouse to set the pointer 80 on an "automatic setting" button 8k on the screen of the display section 8 shown in FIG. 2 and perform the click operation, the parameter is automatically set to a preset value. As a result, the defect extraction can be again effected for each substrate image 81 which has been subjected to the non-defective product/defective product judgment which will be described later. A value of this parameter is reflected on positions of the slide switches 7a and 7b. Moreover, when the inspector uses the mouse to set the pointer 80 to a "return" button 8c on the screen of the display section 8 shown in FIG. 2 and effect the click operation, each substrate image 81 obtained by the parameter before change can be redisplayed. By this operation, the image obtained by the previous parameter can be redisplayed by the single click operation and the image obtained by the last but one parameter can be redisplayed by the double click operation. That is, the image is redisplayed along the parameter change history in accordance with a number of times of clicking. As a result, the inspector can determine an optimum parameter by comparing the image after changing the parameter and the counterpart before changing the parameter.

Thereafter, in the similar manner, the inspector operates the slide switches 7a and 7b to change the parameter and checks a degree that a defect part appears in the substrate images 81 with "OK" displayed on the area 8a or an extent of shift to defect products while adjusting the upper limit value a and the lower limit value b of the threshold value for the defect extraction. In this case, a part extracted as a defective portion by changing the parameter in the image is displayed with its color being changed. For example, the color of the defective portion is changed into an orange color if the defective portion is increased or it is changed into a gray color if it is decreased. In addition, the color of the frame portion 811 of the substrate image 81 whose defective portion is increased may be changed. Additionally, if color coding is carried out in accordance with each type of defects, the density of the defect display color may be changed in accordance with the parameter change history.

After these operations, when the inspector performs the click operation with the pointer 80 being set at an "end" button 8d on the screen of the display section 8 shown in FIG. 2 if the parameter optimum for the defect extraction seems to be obtained, that parameter is determined as a parameter in the defect extraction section 601 for each substrate 2 in units of the initially selected recipe inspection lot. Further, the defective substrate image 82 finally determined as a defective product by the inspector with this parameter is registered.

Incidentally, when the inspector sets the pointer 80 at a "display/non-display" button 8e on the screen of the display section 8 shown in FIG. 2 to carry out the click operation, ON/OFF (display/non-display) of display of the defective portion can be switched. Furthermore, in case of non-display by which the defective portion is not displayed, by emphasizing the contrast of the image on the screen, the inspector can easily see the actual state of the substrate.

Thereafter, as similar to a series of the operations mentioned above, by determining the parameter in the defect extraction section 601 for each substrate 2 in units of other inspection lots, each recipe can be created.

Subsequently, after creating the above-described recipe, the defect detection is executed for the substrate which is an actual inspection target.

Figure 4:
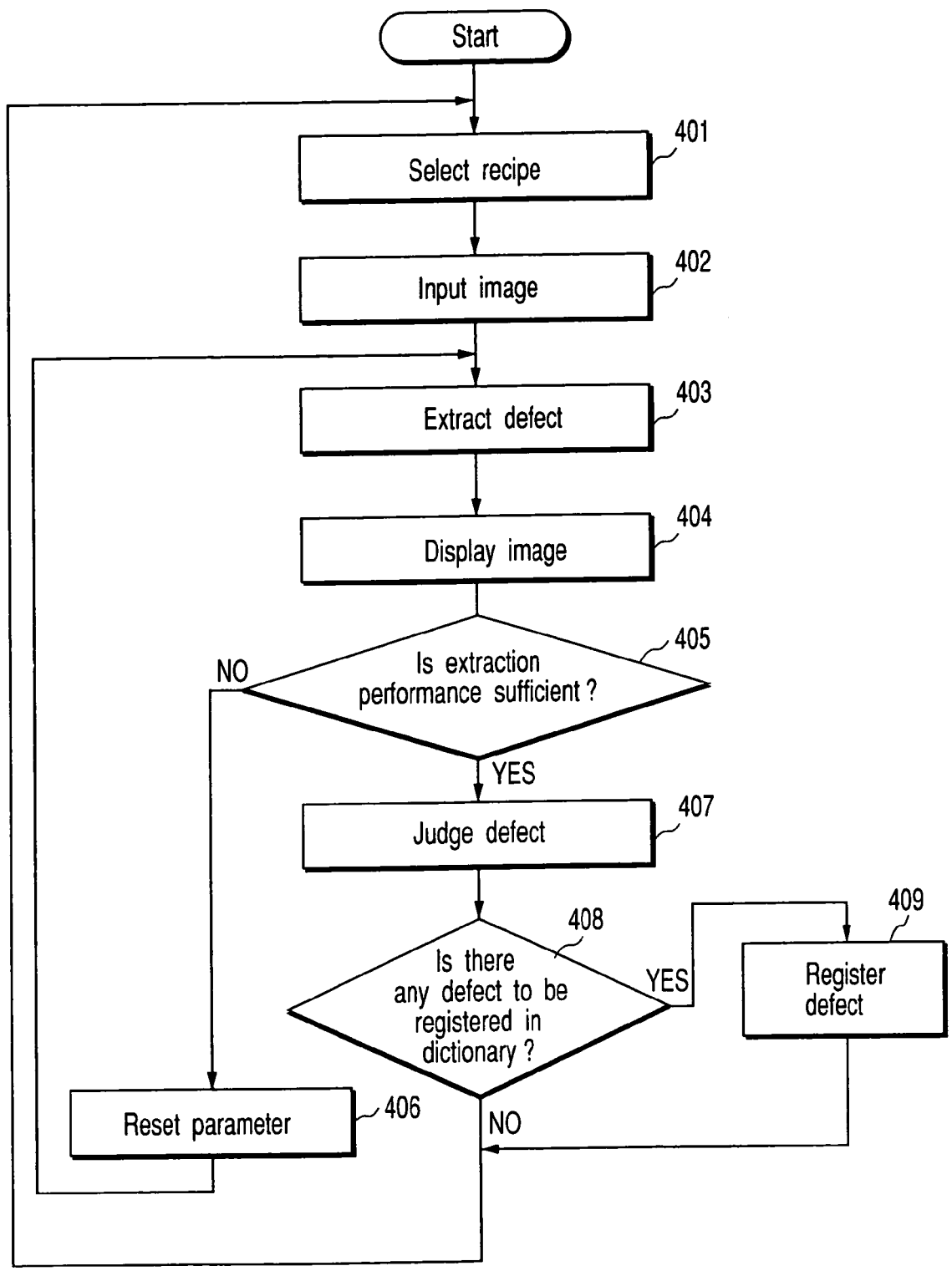
FIG. 4 is a flowchart showing the operation procedure of defect detection by the defect inspection system according to the embodiment of the present invention.

FIG. 4 is a flowchart showing an operation procedure of the defect detection by the defect inspection system. In step 401, the defect extraction section 601 of the control section 6 first selects a recipe according to the inspection lot as an inspection target among a plurality of recipes generated as mentioned above. Then, in step 402, the surface of each substrate 2 of the inspection lot is imaged by the line sensor camera 3, and the picked-up image is generated as a two-dimensional image by the image input section 4. The pixel data of the two-dimensional images is stored in the image storage section 5 and supplied to the defect extraction section 601.

Subsequently, in step 403, the defect extraction section 601 executes the defect extraction of each substrate 2 by using the parameter according to the selected recipe. Thereafter, in step 404, the control section 6 displays the image of each substrate 2 and a result of defect extraction by the defect extraction section 601 as the thumbnail image on the area 8a of the display section 8.

In this case, as similar to FIG. 2, the substrate images 81 of all the substrates 2 of the inspection lot are aligned and displayed on the area 8a of the display section 8 in the order of the slots or ID codes or in the random order in the vertical and horizontal directions. At this time, the substrate image 81 of the substrate 2 from which a defect has been extracted is displayed on such a manner that a defective portion is superimposed on the substrate image 81. On the other hand, as similar to FIG. 2, each defective substrate image 82 from which a defect has been extracted during creation of the above-described recipe or the previous inspection and which has been registered as a defective product is aligned and displayed on the area 8b of the display section 8 in the vertical direction with a defective portion being superimposed thereon. In this state, when the inspector uses the mouse to set the pointer 80 on either the substrate image 81 or 82 displayed on the area 8a or the area 8b and carry out the click operation, only that image can be enlarged and displayed as one-image display.

Then, in step 405, the inspector sees the display section 8 and judges whether the defect extraction performance is sufficient. If it is not sufficient, the parameter for the defect extraction section 601 is changed in step 406. In this case, the inspector changes the parameter by operating the slide switches 7a and 7b displayed on the screen of the display section 8 as described above. As a result, in step 403, the defect extraction section 601 again executes the defect extraction of each substrate 2 by the changed parameter. Then, the processing of the step 404 and the subsequent steps is performed. In this case, it is desirable to record and manage the contents of the changed recipe.

If it is determined that the defect extraction performance is sufficient in step 405, the defect judgment is carried out by inputting a predetermined direction from the input section 7 by the inspector in step 407. In this case, defect information of each substrate 2 is supplied from the defect extraction section 601 to the quality judgment section 9, and the defect judgment is executed in the quality judgment section 9. The quality judgment section 9 checks the defect information with the defect data stored in the defect dictionary 10 and determines a type and the like of a defect extracted by the defect extraction section 601. Further, the quality judgment section 9 judges whether each substrate 2 can be put in the next production line, namely, upon the quality (non-defective product/defective product) of each substrate 2 based on the judgment result. The defect judgment and the quality judgment may be carried out by watching the later-described screen of the display section 8 by the inspector.

Figure 5:
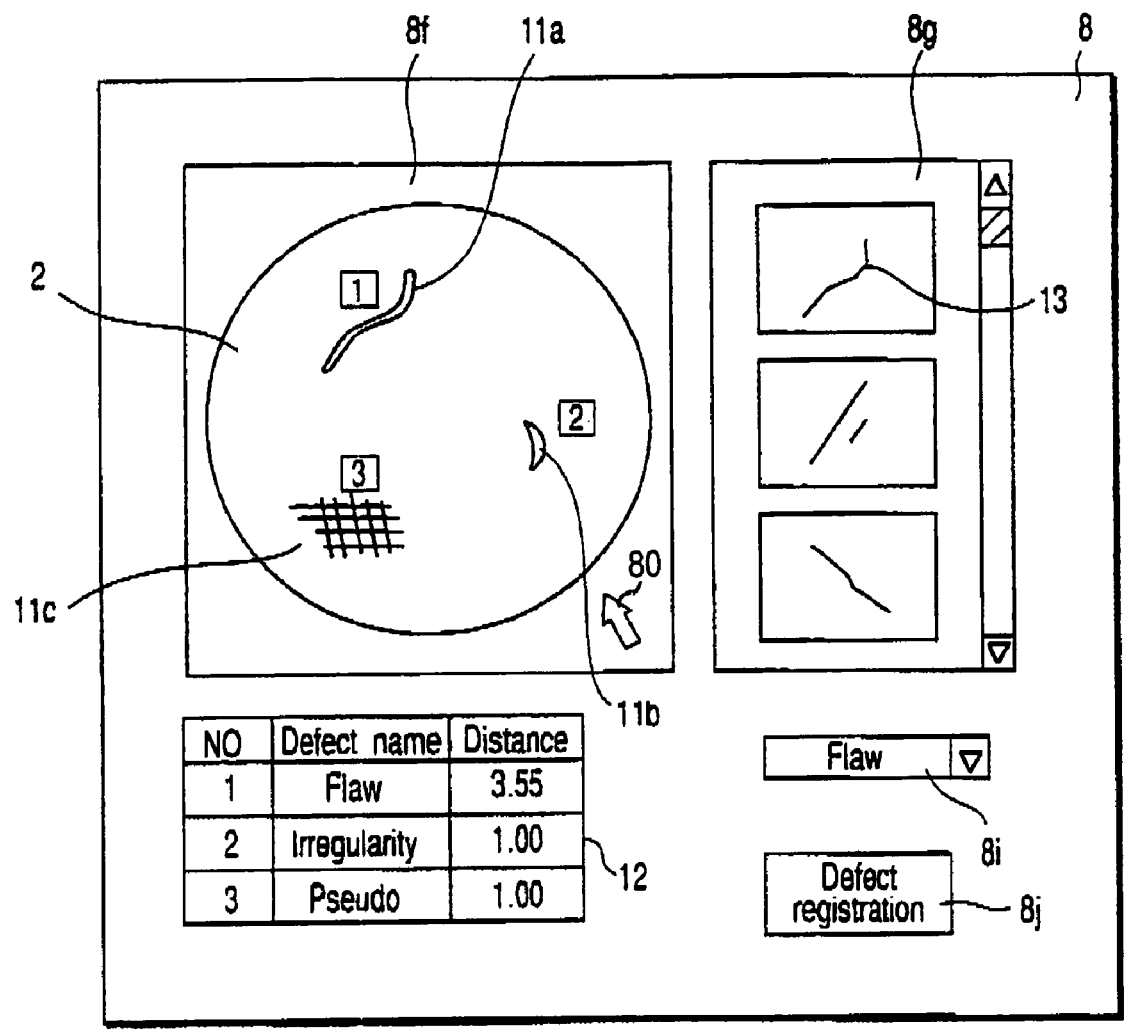
FIG. 5 is a view showing a display example on the display section at the time of defect judgment according to the embodiment of the present invention.

FIG. 5 is a view showing a display example of on the display section 8 at the time of above-described defect judgment. The defective portions 11a, 11b and 11c are superimposed on the image of the substrate 2 and displayed on the area 8f which is provided at the substantially central portion of the screen. In the lower left portion of the area 8f is displayed a list 12 on which types (defect names) and assurance (distribution values (distances)) of the defects as the defect judgment reference) of the respective defective portions 11a, 11b and 11c are written. Images of the respective defects 13 registered in the defect dictionary 10 are aligned and displayed on the area 8g on the right side of the screen in the vertical direction. Images of other defects 13 (not shown in FIG. 5) can be displayed by scrolling the area 8g. The respective defective portions 11a, 11b and 11c may be displayed and distinguished by using different colors in accordance with types of the defects. A length, a radius, a contrast, an orientation, circularity, a width, a position and others may be displayed on the list 12 as characteristic quantities of various defects as well as a distance (distribution value).

In this case, the inspector can use the mouse to set the pointer 80 at a predetermined position on the screen of the display section 8 and perform the click operation, thereby minimizing or enlarging the entire image on the area 8f. In addition, when the inspector uses the mouse to set the pointer 80 at any one of the defective portions 11a, 11b and 11c or an arbitrary defect name in the list 12 and carry out the click operation, a corresponding type of each defect 13 is displayed on the area 8g. Additionally, when the inspector selects another type of defect displayed on a defect type change box 8i consisting of a drop-down list box on the screen of the display section 8, the displayed defect on the area 8g is changed to a corresponding type of defect. That is, each defect corresponding to each type of defect displayed on the defect type change box 8i is previously registered in the defect dictionary 10. When the inspector designates any type of defect, each defect corresponding to that type of defect is read from the defect dictionary 10 and displayed on the area 8g. Further, when the inspector clicks a predetermined defect 13 on the area 8g, the entire image of the substrate 2 on which that defect is generated is displayed. As a result, it is possible to recognize a position or a direction of the defect on the entire substrate.

Subsequently, in step 408, the defect extraction section 601 judges whether there is defect information which should be newly registered in the defect dictionary 10 among the defect information of each substrate 2. Here, if there is the defect information to be newly registered, the defect extraction section 601 registers it in the defect dictionary 10 in step 409. The defect registration may be carried out from the input section 7 by watching the screen of the display section 8 by the inspector. In this case, for example, the inspector uses the mouse to set the pointer 80 at any one, which should be newly registered, of the defective portions 11a, 11b and 11c displayed on the area 8f in FIG. 5 and perform the click operation in order to select a desired portion. Further, the inspector clicks a "defect registration" button 8j. As a result, information of the selected defective portion is newly registered from the defect extraction section 601 to the defect dictionary 10. Registration in the defect dictionary 10 is enabled by moving one which should be newly registered among the defective portions 11a, 11b and 11c to the area 8g by the drag & drop operation. Furthermore, a plurality of defects may be temporarily registered by the drag & drop operation in advance, and they may be collectively registered by clicking the "defect registration" button 8j when the defects to be registered are finally determined.

Thereafter, by repeatedly executing a series of the above-described operations while replacing the inspection lot as an inspection target, the defect inspection of the surface of each substrate is conducted, and new defects are registered.

According to this embodiment, the surface images of a plurality of substrates 2 are displayed on the same screen of the display section 8 in units of the inspection lot. In this state, the parameter for the defect extraction section 601 is changed by the upper limit value slide switch 7a and the lower limit value slide switch 7b of the input section 7, and the upper limit value and the lower limit value of the threshold value for defect extraction, i.e., the defect extraction sensitivity is thereby adjusted. The optimum environment for defect extraction is set while visually confirming a degree of a defective portion which appears in the surface image of each substrate 2 by the inspector based on this adjustment. As a result, the recipe for defect extraction can be easily created with high reliability.

In addition, by preparing the parameter inputted from the input section 7 in accordance with types of defects such as flaws, irregularities, dust and others, the highly accurate defect extraction environment can be set. Further, since defective portion is displayed so as to be superimposed on the surface image of the substrate 2 displayed on the display section 8, a position of the defective portion on the surface of the substrate 2 can be accurately grasped.

Furthermore, the abnormality in the process can be specified based on a result of the quality judgment of the substrate 2 as a inspection subject, and it is possible to make judgment upon whether the substrate 2 should be shifted to the next process or returned to the previous process.

The present invention is not limited to the above-described embodiment and can be modified within the scope of the invention.

According to the present invention, the operation for creating the recipe for defect extraction can be readily carried out, and it is possible to provide the defect inspection system capable of creating the recipe with high reliability.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A defect inspection system comprising:
   an image acquiring section for acquiring a two-dimensional image of an entire surface of each of a plurality of subjects;
   an image storing section for storing, as image data, the two-dimensional image of the entire surface of said each subject acquired by said image acquiring section;
   a defect extracting section for extracting defect data of the surface of said each subject based on a defect extraction algorithm using a predetermined parameter for the two-dimensional image read out from said image storing section, so as to extract a defect if the defect is determined to be present based on the defect extraction algorithm;
   a displaying section for displaying an image of each defect extracted by said defect extracting section, by superimposing the image of the defect on the two-dimensional image of a subject which is determined to have the defect;

a parameter adjusting section for adjusting the parameter to set a new parameter to change a defect extraction degree for said each subject; and a quality judging section for judging whether said each subject is acceptable, by checking the defect data extracted by said defect extracting section with reference to defect data registered in advance in a defect dictionary, wherein when the parameter is adjusted by the parameter adjusting section:

said displaying section displays two kinds of two-dimensional images including at least one said two-dimensional image acquired by the image acquiring section when inspection is performed and a two-dimensional image of a subject which has been registered in advance as defective;

said defect extracting section extracts updated defect data based on the defect extraction algorithm using the new parameter adjusted by the parameter adjusting section for the two kinds of two-dimensional images; and said display section displays each updated defect which is determined to exist based on the updated defect data extracted by said defect extracting section, by superimposing an image of the updated defect on corresponding images of the two kinds of two-dimensional images displayed by said displaying section.

2. The defect inspection system according to claim 1, wherein said displaying section has a function of reducing sizes of two-dimensional images of the plurality of subjects subjected to defect extracting processing by said defect extracting section, and of displaying the two-dimensional images, and a function of displaying results of judgment by said quality judging section using at least one of color and characters, with respect to the two-dimensional images of the plurality of subjects.

3. The defect inspection system according to claim 1, wherein said displaying section has a function of displaying thumbnail images obtained by reducing sizes of two-dimensional images of the plurality of subjects subjected to defect extraction processing by said defect extracting section, a function of enlarging and displaying a specified one of the thumbnail images, and a function of specifying a defect portion on said specified one of the thumbnail images to thereby display a kind of a defect which corresponds to the defect portion.

4. The defect inspection system according to claim 1, wherein said displaying section has a function of reducing sizes of two-dimensional images of the plurality of subjects subjected to defect extraction processing by said defect extracting section, and of displaying the two-dimensional images of the plurality of subjects such that the two-dimensional images of the plurality of subjects are discriminated from each other with respect to whether said quality judging section has judged a subject corresponding to the two-dimensional image to be acceptable.

5. The defect inspection system according to claim 1, wherein said displaying section displays the image of the updated defect extracted in accordance with the new parameter with a color of the image of the updated defect changed in accordance with an extraction degree corresponding to the new parameter.

6. The defect inspection system according to claim 1, wherein said displaying section changes a color of the image of the updated defect, in accordance with a change history of the parameter adjusted by said parameter adjusting section.

7. The defect inspection system according to claim 1, wherein said displaying section has a function of displaying a re-displaying button for changing the new parameter adjusted by said parameter adjusting section back to a former parameter, and a function of re-displaying the two-dimensional image of said each subject based on the former parameter, when the re-displaying button is clicked.

8. A defect inspection system comprising:

an image acquiring section for acquiring a two-dimensional image of an entire surface of a subject which is a processing target in a manufacturing process;

an image storing section for storing, as image data, the two-dimensional image of the entire surface of the subject acquired by said image acquiring section;

a defect extracting section for extracting, as defect data, a defect of the surface of the subject based on a defect extraction algorithm using a predetermined parameter for the two-dimensional image read out from said image storing section;

a displaying section for displaying an image of the defect of the subject extracted by said defect extracting section, as a defect image of the subject;

a parameter adjusting section for adjusting the parameter to change a defect extraction degree for the defect image of the subject displayed by said displaying section; and a quality judging section for judging whether the subject is good or bad, by checking defect data extracted by said defect extracting section with reference to defect data registered in advance in a defect dictionary;

wherein said defect extracting section extracts, as defect data, a defect of the subject based on a defect extraction algorithm using a new parameter adjusted by said parameter adjusting section, and updates the defect image displayed by said displaying section;

wherein said displaying section has a function of displaying a re-displaying button for changing the parameter adjusted by said parameter adjusting section back to a former parameter, and a function of re-displaying the defect image extracted based on the former parameter, when the re-displaying button is clicked; and wherein said displaying section has a function of comparing images respectively obtained based on the parameter adjusted by said parameter adjusting section and the former parameter, and of displaying a determination button for determining one of the parameters as an optimal parameter.

9. The defect inspection system according to claim 1, wherein said quality judging section has a function of determining a kind of the defect by checking the defect data extracted by said defect extracting section with reference to the defect data registered in advance in the defect dictionary, and a function of registering new defect data in the defect dictionary.

10. The defect inspection system according to claim 1, wherein said defect extracting section produces a recipe for determining the defect extraction degree, which serves as a reference for judging whether the subject is acceptable.

11. The defect inspection system according to claim 1, wherein a parameter for selecting a subject recognized in advance to be good is automatically set in said defect extracting section.

12. The defect inspection system according to claim 1, wherein said parameter adjusting section is adapted to set upper and lower limit values of the parameter as threshold values for defect extraction.

13. The defect inspection system according to claim 12, wherein said displaying section displays two-dimensional images of the plurality of subjects as thumbnail images.

14. The defect image inspection system according to claim 12, wherein said defect extracting section extracts, from data exceeding the lower limit value, data exceeding the upper limit value as the defect data.

15. A defect image inspection system comprising:
an image acquiring section for acquiring a two-dimensional image of an entire surface of a subject which is a processing target in a manufacturing process;
an image storing section for storing, as image data, the two-dimensional image of the entire surface of the subject acquired by said image acquiring section;
a defect extracting section for extracting, as defect data, a defect of the surface of the subject based on a defect extraction algorithm using a predetermined parameter for the two-dimensional image read out from said image storing section;
a displaying section for displaying an image of the defect of the subject extracted by said defect extracting section, as a defect image of the subject;
a parameter adjusting section for adjusting the parameter to chance a defect extraction degree for the defect image of the subject displayed by said displaying section; and
a quality judging section for judging whether the subject is acceptable, by checking defect data extracted by said defect extracting section with reference to defect data registered in advance in a defect dictionary;
wherein said defect extracting section extracts, as defect data, a defect of the subject based on a defect extraction algorithm using a new parameter adjusted by said parameter adjusting section, and updates the defect image displayed by said displaying section;
wherein said parameter adjusting section is adapted to set upper and lower limit values of the predetermined parameter as threshold values for defect extraction, said defect extracting section extracts, as the defect data, the defect of the subject based on the defect extraction algorithm using the new parameter adjusted by said parameter adjusting section, and said displaying section displays the defect image extracted by said defect extracting section, after updating the defect image; and
wherein said displaying section displays a slide switch for setting the upper and lower limit values in an area other than a defect image displaying area on a screen.

16. The defect image inspection system according to claim 1, wherein said defect extracting section prepares a plurality of respective groups of parameters for kinds of defects, kinds of inspection conditions, kinds of inspection methods and kinds of extraction methods, and said parameter adjusting section adjusts the parameters of each of the groups.

* * * * *